US012245896B2

(12) United States Patent
Toporek

(10) Patent No.: US 12,245,896 B2
(45) Date of Patent: Mar. 11, 2025

(54) DEEP LEARNING-BASED ULTRASOUND IMAGING GUIDANCE AND ASSOCIATED DEVICES, SYSTEMS, AND METHODS

(71) Applicant: KONINKLIJKE PHILIPS N.V., Eindhoven (NL)

(72) Inventor: Grzegorz Andrzej Toporek, Boston, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 333 days.

(21) Appl. No.: 17/285,124

(22) PCT Filed: Oct. 16, 2019

(86) PCT No.: PCT/EP2019/078079
§ 371 (c)(1),
(2) Date: Apr. 14, 2021

(87) PCT Pub. No.: WO2020/079077
PCT Pub. Date: Apr. 23, 2020

(65) Prior Publication Data
US 2021/0369249 A1    Dec. 2, 2021

Related U.S. Application Data

(60) Provisional application No. 62/746,042, filed on Oct. 16, 2018.

(51) Int. Cl.
*G16H 30/20* (2018.01)
*A61B 8/00* (2006.01)
*A61B 8/08* (2006.01)

(52) U.S. Cl.
CPC .......... *A61B 8/5292* (2013.01); *A61B 8/4263* (2013.01); *A61B 8/465* (2013.01);
(Continued)

(58) Field of Classification Search
None
See application file for complete search history.

(56) References Cited

U.S. PATENT DOCUMENTS 6,491,632 B1 * 12/2002 Taylor ..................... G06T 17/00
                                                    600/443
2013/0218024 A1 * 8/2013 Boctor ................. A61B 5/0077
                                                    600/476
(Continued)

FOREIGN PATENT DOCUMENTS

EP          3332712 A1    6/2018
JP       2010279486 A    12/2010
(Continued)

OTHER PUBLICATIONS

PCT/EP2019/078079 ISR & Wrtten Opinion, Feb. 12, 2020, 13 Page Document.

*Primary Examiner* — Serkan Akar
*Assistant Examiner* — Aminah Asghar

(57) ABSTRACT

Ultrasound imaging devices, systems, and methods are provided. A guidance system for obtaining an ultrasound image, comprising a processor in communication with a camera and a display, the processor configured to obtain a first motion control configuration for repositioning an ultrasound imaging device from a first position towards a target image view of a subject's anatomy, the first motion control configuration determined based on a first predictive network; determine positional information associated with the ultrasound imaging device based on an image captured by the camera, the image including the subject's anatomy and the ultrasound imaging device positioned at the first position; and output, to the display, an instruction to reposition the ultrasound imaging device from the first position to a
(Continued)

second position based on the first motion control configuration and the positional information associated with the ultrasound imaging device.

17 Claims, 13 Drawing Sheets

(52) U.S. Cl.
CPC ............ *A61B 8/5215* (2013.01); *A61B 8/585* (2013.01); *G16H 30/20* (2018.01)

(56) References Cited

U.S. PATENT DOCUMENTS

| | | |
|---|---|---|
| 2017/0360401 A1 | 12/2017 | Rothberg et al. |
| 2017/0360402 A1 | 12/2017 | de Jonge et al. |
| 2017/0360403 A1 | 12/2017 | Rothberg et al. |
| 2018/0153505 A1* | 6/2018 | Cadieu ................. A61B 8/4254 |
| 2018/0368686 A1* | 12/2018 | Punithakumar ...... A61B 5/0035 |

FOREIGN PATENT DOCUMENTS

| | | |
|---|---|---|
| JP | 2018134386 A | 8/2018 |
| WO | 2015150932 A1 | 10/2015 |
| WO | 2019174953 A1 | 9/2019 |
| WO | 2019175129 A1 | 9/2019 |

* cited by examiner

DEEP LEARNING-BASED ULTRASOUND IMAGING GUIDANCE AND ASSOCIATED DEVICES, SYSTEMS, AND METHODS

CROSS-REFERENCE TO PRIOR APPLICATIONS

This application is the U.S. National Phase application under 35 U.S.C. § 371 of International Application No. PCT/EP2019/078079, filed on Oct. 16, 2019, which claims the benefit of U.S. Provisional Patent Application No. 62/746,042, filed on Oct. 16, 2018. These applications are hereby incorporated by reference herein.

TECHNICAL FIELD

The present disclosure relates generally to ultrasound imaging and, in particular, to providing visual guidance or feedback for positioning an ultrasound transducer to a desired imaging plane.

BACKGROUND

Ultrasound imaging is a noninvasive medical test that helps physicians diagnose and treat medical conditions. Ultrasound imaging uses high-frequency sound waves to produce images of tissues, organs, and/or blood flows within a human body. An ultrasound imaging system may include an ultrasound transducer or transducer array that can be excited or triggered to send sound waves towards a target body part (e.g., tissues and organs) and records the echoes reflected back, thus defining the size, shape and mass of the target body part. The ultrasound imaging system may use a variety of imaging modes, such as B-mode and Doppler flow. For B-mode imaging, the ultrasound imaging system may create two-dimensional images of tissue in which the brightness of a pixel is based on the intensity of the reflected echo. For Doppler flow imaging, the ultrasound system may determine the movement of fluid (e.g., blood) or tissue based on a Doppler effect, where the reflected echoes are shifted in frequency with respect to the incident wave.

Recently, point-of-care (POC) ultrasound imaging at bedside has gained popularity in intensive care units (ICUs) and emergency situations for various types of diagnostics, for example, for diagnoses related to the heart, liver, and/or lung. In a POC ultrasound imaging system, the ultrasound transducer may be in the form of a handheld ultrasound probe connecting to a mobile device, where ultrasound images may be displayed on the mobile device. During a clinical assessment, a clinician may move the handheld probe along a Cartesian plane to locate an optimal imaging view for imaging a certain anatomy for the assessment. However, due to the multiple degrees of freedom at the probe, it may be time-consuming and challenging for a clinician to find the optimal view. Foreshortened viewing planes or imaging planes can lead to misdiagnosis and/or unnecessary repetition of an examination.

SUMMARY

While existing ultrasound imaging has proved useful for clinical examinations and diagnosis, there remains a clinical need for improved systems and techniques for providing efficient, accurate, and automatic procedures for aligning an imaging component to a desired imaging plane. Embodiments of the present disclosure provide a hybrid automatic probe positioning guidance approach to assist and guide a user in positioning an ultrasound imaging probe to an optimal position for an ultrasound examination. The disclosed embodiments utilize a deep learning network to provide imaged-based motion prediction with camera tracking to improve the accuracy of the motion prediction. For example, a clinician may position an imaging probe at a first position with respect to a patient's anatomy of interest and capture an ultrasound image of the patient's anatomy. At the same time, a camera can capture camera images of the imaging probe and the patient. A deep learning network can be applied to the ultrasound image to predict a first motion control configuration for maneuvering the imaging probe towards a desired imaging view. A tracking algorithm can be applied to the camera image to determine a second motion control configuration for maneuvering the imaging probe towards a desired imaging view. The disclosed embodiments combine the first motion control configuration from the deep learning and the second motion control configuration from the tracking to provide the automatic probe guidance. The combining can improve the accuracy of the automatic probe guidance. The disclosed embodiments may display probe guidance instructions using a graphical representation overlaid on the camera images in real-time. The disclosed embodiments can further improve the deep learning-based motion detection by filtering out image data that are irrelevant and/or of poor image quality prior to applying the deep learning network. The filtering of image data can reduce the complexity of the deep learning network and/or improve performance of the deep learning-based motion prediction. The disclosed embodiments can be applied to any ultrasound imaging system.

In one embodiment, a guidance system for obtaining an ultrasound image, comprising a processor in communication with a camera and a display, the processor configured to obtain a first motion control configuration for repositioning an ultrasound imaging device from a first position towards a target image view of a subject's anatomy, the first motion control configuration determined based on a first predictive network; determine positional information associated with the ultrasound imaging device based on an image captured by the camera, the image including the subject's anatomy and the ultrasound imaging device positioned at the first position; and output, to the display, an instruction to reposition the ultrasound imaging device from the first position to a second position based on the first motion control configuration and the positional information associated with the ultrasound imaging device.

In some embodiments, wherein the first predictive network represents the first position based on a first coordinate system, wherein the image captured by the camera represents the first position based on a second coordinate system, wherein the processor is configured to determining a coordinate system transformation between the first coordinate system and the second coordinate system based on the positional information; determine a second motion control configuration based on the first motion control configuration and the coordinate system transformation; and determining the instruction based on the first motion control configuration and the second motion control configuration. In some embodiments, wherein the processor is configured to determine the instruction by combining the first motion control configuration and the second motion control configuration. In some embodiments, wherein the processor is configured to determine the instruction based on a comparison between the first motion control configuration and the second motion control configuration. In some embodiments, wherein the ultrasound imaging device is coupled to a marker, wherein the image includes the marker, and wherein the processor is configured to determine the coordinate system transformation based on a relative position between the ultrasound imaging device and the marker. In some embodiments, wherein the processor is configured to determine the coordinate system transformation based on a relative position between the camera and the subject's anatomy. In some embodiments, wherein the processor is configured to determine the coordinate system transformation based on a relative position between the camera and a marker positioned on the subject. In some embodiments, wherein the first control motion configuration includes at least one of a first rotation or a first translation. In some embodiments, wherein the processor is configured to output the instruction to display the image including the subject's anatomy and the ultrasound imaging device; and an overlay of a graphical representation of at least one of a rotation or a translation for repositioning the ultrasound imaging device to the second position. In some embodiments, the system of claim further comprises the camera; and the display. In some embodiments, the system further comprises a mobile device including the camera, the processor, and the display. In some embodiments, wherein the processor is in communication with the ultrasound imaging device, and wherein the processor is configured to obtain the first motion control configuration by receiving, from the ultrasound imaging device, an ultrasound image representative of the subject's anatomy while the ultrasound imaging device is positioned at the first position; and applying the first predictive network to the ultrasound image to produce the first motion control configuration. In some embodiments, wherein the processor is configured to obtain the first motion control configuration by applying the first predictive network to a region of interest (ROI) of the ultrasound image to produce the first motion control configuration. In some embodiments, wherein the processor is configured to obtain the first motion control configuration by at least one of receiving, from a user interface in communication with the processor, a selection of the ROI; or determining the ROI based on a second predictive network. In some embodiments, wherein the processor is configured to obtain the first motion control configuration by applying the first predictive network to determine a region of interest (ROI) within the ultrasound image and to determine the first motion control configuration based on the determined ROI.

In one embodiment, a method of providing ultrasound imaging guidance, the method comprising obtaining a first motion control configuration for repositioning an ultrasound imaging device positioned from a first position towards a target image view of a subject's anatomy, the first motion control configuration determined based on a first predictive network; determining positional information associated with the ultrasound imaging device based on an image captured by a camera, the image including the subject's anatomy and the ultrasound imaging device positioned at the first position; and displaying, on a display, an instruction to reposition the ultrasound imaging device from the first position to a second position based on the first motion control configuration and the positional information associated with the ultrasound imaging device.

In some embodiments, wherein the first predictive network represents the first position based on a first coordinate system, wherein the image captured by the camera represents the first position based on a second coordinate system, wherein the method further comprises determining a coordinate system transformation between the first coordinate system and the second coordinate system based on the positional information; and determining the instruction based on at least the first motion control configuration and the coordinate system transformation. In some embodiments, the method further comprises determining a second motion control configuration based on the first motion control configuration and the coordinate system transformation; and determining the instruction by applying at least one of a combining function to the first motion control configuration and the second motion control configuration; or a comparison function to the first motion control configuration and the second motion control configuration. In some embodiments, wherein the ultrasound imaging device is coupled to a marker, wherein the image includes the marker, and wherein the method further comprises determining the coordinate system transformation based on a relative position between the ultrasound imaging device and the marker. In some embodiments, the method of further comprises determining the coordinate system transformation based on a relative position between the camera and the subject's anatomy.

Additional aspects, features, and advantages of the present disclosure will become apparent from the following detailed description.

BRIEF DESCRIPTION OF THE DRAWINGS

Illustrative embodiments of the present disclosure will be described with reference to the accompanying drawings, of which.

DETAILED DESCRIPTION

Figure 1:
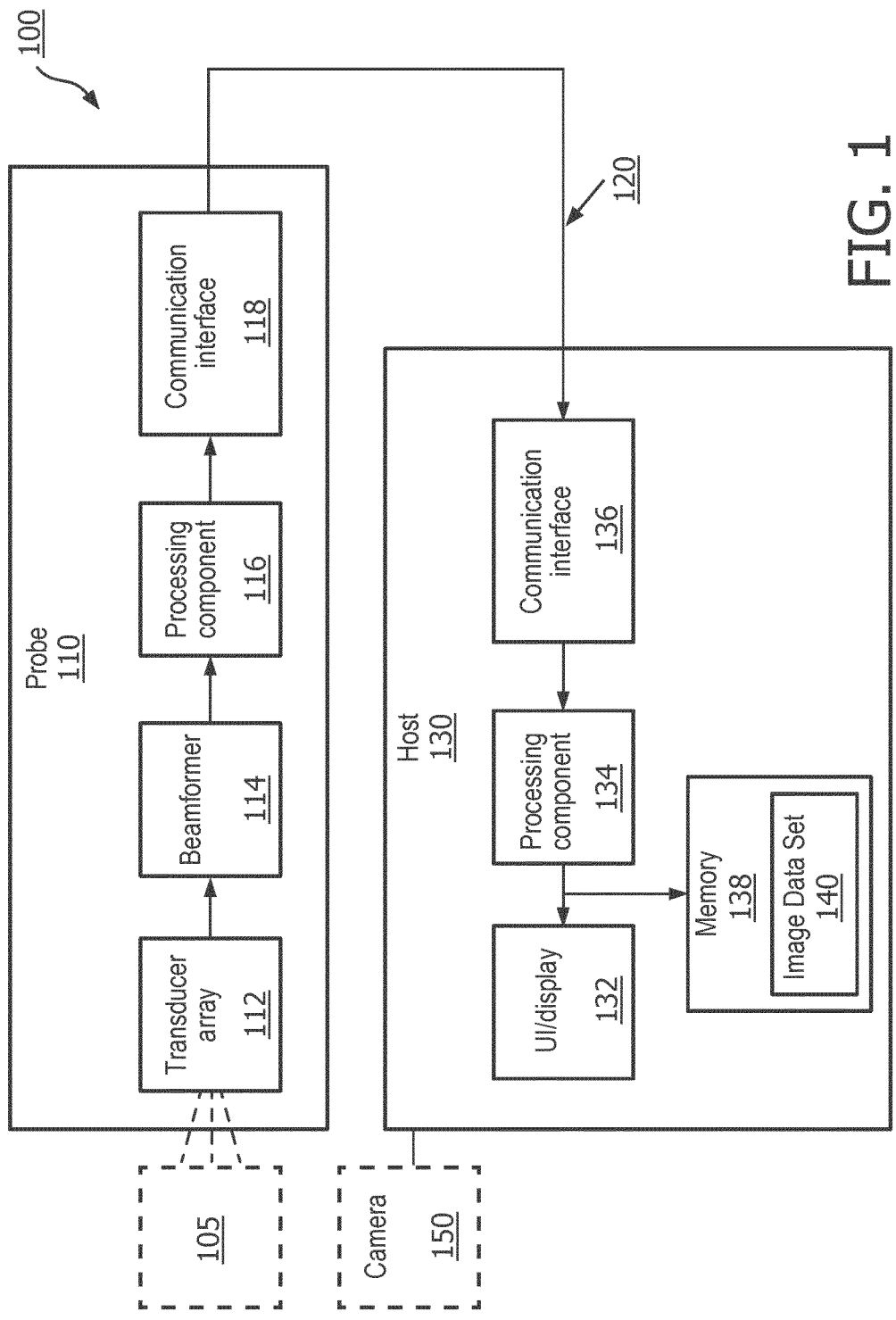
FIG. 1 is a schematic diagram of an ultrasound imaging system, according to aspects of the present disclosure.

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

FIG. 1 is a schematic diagram of an ultrasound imaging system 100, according to aspects of the present disclosure. The system 100 is used for scanning an area or volume of a patient's body. The system 100 includes an ultrasound imaging probe 110 in communication with a host 130 over a communication interface or link 120. The probe 110 includes a transducer 112, a beamformer 114, a processing component 116, and a communication interface 118. The host 130 includes a user interface (UI)/display 132, a processing component 134, and a communication interface 136.

The probe 110 may be in any suitable form for imaging various body parts of a patient while positioned inside or outside of the patient's body. In an embodiment, the probe 110 is an external ultrasound imaging device including a housing configured for handheld operation by a user. The transducer 112 can be configured to obtain ultrasound data while the user grasps the housing of the probe 110 such that the transducer 112 is positioned adjacent to and/or in contact with a patient's skin. The probe 110 is configured to obtain ultrasound data of anatomy within the patient's body while the probe 110 is positioned outside of the patient's body. In some other embodiments, the probe 110 may be in the form of a catheter, an intravascular ultrasound (IVUS) catheter, an intracardiac echocardiography (ICE) catheter, a transesophageal echocardiography (TEE) probe, a transthoracic echocardiography (TTE) probe, an endo-cavity probe, a handheld ultrasound scanner, or a patch-based ultrasound device.

The transducer 112 emits ultrasound signals towards an anatomical object 105 and receives echo signals reflected from the object 105 back to the transducer 112. The ultrasound transducer 112 can include any suitable number of acoustic elements, including one or more acoustic elements and/or plurality of acoustic elements. In some instances, the transducer 112 includes a single acoustic element. In some instances, the transducer 112 may include an array of acoustic elements with any number of acoustic elements in any suitable configuration. For example, the transducer 112 can include between 1 acoustic element and 1000 acoustic elements, including values such as 2 acoustic elements, 4 acoustic elements, 36 acoustic elements, 64 acoustic elements, 128 acoustic elements, 500 acoustic elements, 812 acoustic elements, and/or other values both larger and smaller. In some instances, the transducer 112 may include an array of acoustic elements with any number of acoustic elements in any suitable configuration, such as a linear array, a planar array, a curved array, a curvilinear array, a circumferential array, an annular array, a phased array, a matrix array, a one-dimensional (1D) array, a 1.x dimensional array (e.g., a 1.5D array), or a two-dimensional (2D) array. The array of acoustic elements (e.g., one or more rows, one or more columns, and/or one or more orientations) that can be uniformly or independently controlled and activated. The transducer 112 can be configured to obtain one-dimensional, two-dimensional, and/or three-dimensional images of patient anatomy. In some embodiments, the transducer 112 may include a piezoelectric micromachined ultrasound transducer (PMUT), capacitive micromachined ultrasonic transducer (CMUT), single crystal, lead zirconate titanate (PZT), PZT composite, other suitable transducer types, and/or combinations thereof.

The beamformer 114 is coupled to the transducer 112. The beamformer 114 controls the transducer 112, for example, for transmission of the ultrasound signals and reception of the ultrasound echo signals. The beamformer 114 provides image signals to the processing component 116 based on the response or the received ultrasound echo signals. The beamformer 114 may include multiple stages of beamforming. The beamforming can reduce the number of signal lines for coupling to the processing component 116. In some embodiments, the transducer 112 in combination with the beamformer 114 may be referred to as an ultrasound imaging component.

In some embodiments, the object 105 may include at least a portion of a patient's heart for heart performance assessment. In other embodiments, the object 105 may include any anatomy (e.g., lung, blood vessel, heart, kidney, and/or liver) of a patient that is suitable for ultrasound imaging examination.

The processing component 116 is coupled to the beamformer 114. The processing component 116 may include a central processing unit (CPU), a digital signal processor (DSP), an application specific integrated circuit (ASIC), a controller, a field programmable gate array (FPGA) device, another hardware device, a firmware device, or any combination thereof configured to perform the operations described herein. The processing component 134 may also be implemented as a combination of computing devices, e.g., a combination of a DSP and a microprocessor, a plurality of microprocessors, one or more microprocessors in conjunction with a DSP core, or any other such configuration. The processing component 116 is configured to process the beamformed signals. For example, the processing component 116 may perform filtering and/or quadrature demodulation to condition the image signals. The processing component 116 and/or 134 can be configured to control the transducer 112 to obtain ultrasound data associated with the object 105.

The communication interface 118 is coupled to the processing component 116. The communication interface 118 may include one or more transmitters, one or more receivers, one or more transceivers, and/or circuitry for transmitting and/or receiving communication signals. The communication interface 118 can include hardware components and/or software components implementing a particular communication protocol suitable for transporting signals over the communication link 120 to the host 130. The communication interface 118 can be referred to as a communication device or a communication interface module.

The communication link 120 may be any suitable communication link. For example, the communication link 120 may be a wired link, such as a universal serial bus (USB) link or an Ethernet link. Alternatively, the communication link 120 may be a wireless link, such as an ultra-wideband (UWB) link, an Institute of Electrical and Electronics Engineers (IEEE) 802.11 WiFi link, or a Bluetooth link.

At the host 130, the communication interface 136 may receive the image signals. The communication interface 136 may be substantially similar to the communication interface 118. The host 130 may be any suitable computing and display device, such as a workstation, a personal computer (PC), a laptop, a tablet, a mobile phone, handheld personal computer, a mobile device, and/or an ultrasound console.

The processing component 134 is coupled to the communication interface 136. The processing component 134 may be implemented as a combination of software components and hardware components. The processing component 134 may include a central processing unit (CPU), a graphics processing unit (GPU), a digital signal processor (DSP), an application-specific integrated circuit (ASIC), a controller, a FPGA device, another hardware device, a firmware device, or any combination thereof configured to perform the operations described herein. The processing component 134 may also be implemented as a combination of computing devices, e.g., a combination of a DSP and a microprocessor, a plurality of microprocessors, one or more microprocessors in conjunction with a DSP core, or any other such configuration. The processing component 134 can be configured to generate image data from the image signals received from the probe 110. The processing component 134 can apply advanced signal processing and/or image processing techniques to the image signals. In some embodiments, the processing component 134 can form three-dimensional (3D) volume image from the image data. In some embodiments, the processing component 134 can perform real-time processing on the image data to provide a streaming video of ultrasound images of the object 105.

In some embodiments, the processing component 134 can provide automatic guidance in positioning the probe 110 to a position for capturing an optimal view of the object 105. The processing component 134 can apply deep-learning-based techniques (e.g., a predictive network) to determine a motion control configuration or movement vectors (e.g., a rotation and/or a translation) for maneuvering the probe 110 from a current position to an optimal position based on a current imaging view at the current position and a target imaging view including a certain clinical property for an examination, as described in greater detail herein.

In some embodiments, the system 100 includes a camera 150 coupled to the host 130 or integrated within the host 130. During an ultrasound examination, the camera 150 can be configured to capture images of the probe 110 and the patient under the ultrasound examination. The processing component 134 can be configured to track the positioning of the probe 110 with respect to the patient (e.g., a certain body part or anatomy of the patient under examination). The processing component 134 can use the predictive network to generate a motion control configuration for maneuvering the probe 110, track information generated from the image captured by the camera 150, and generate instructions to guide a clinician to move the probe 110 to an optimal view for the ultrasound examination based on the motion control configuration and the camera tracking information, as described in greater detail herein.

The UI/display 132 is coupled to the processing component 134. The display 132 may be a monitor or any suitable display. The UI/display 132 is configured to display ultrasound images, camera-captured images, and/or instructions for positioning the probe 110 to obtain an optimal imaging view in real-time, as described in greater detail herein.

In an embodiment, the system 100 is a POC system. The host 130 may be a tablet, smart phone, and/or other suitable mobile device including a built-in digital camera 150 and an integrated UI/display 132. For example, the POC may be in an ICU, ER, outside of a hospital/clinic in an emergency situation, etc. In other embodiments, the system 100 is an imaging system configured for use in a hospital room or clinic setting other than POC. In an embodiment, the system 100 is a POC echocardiography system. POC echocardiography refers to a focused, goal-directed, transthoracic echocardiogram performed at the patient's bedside by the treating physician to answer specific clinical questions. POC ultrasound (POCUS) can provide several benefits. For instance, POCUS gives emergency physicians (EPs) access to real-time clinical information that can help reduce time to diagnosis. Time is always a precious resource in the emergency department (ED). Fast and accurate bedside ultrasound examination can help avoid severe complications and let the point-of-care physicians transfer patient to a specialized department for further evaluation.

In an embodiment, the system 100 may operate in a server-client environment, where the host 130 may be a server located at a remote location different than a location of the patient and where images of the patient are acquired. The server can receive the acquired images and determine probe guidance instructions by applying a deep learning network. The UI/display 132 may be a separate device from the host 130. For example, the UI/display 132 can be a tablet. The UI/display 132 can be located at the patient's location. The UI/display 132 can execute a web client application in communication with the server. The web client application can receive probe guidance instructions from the server and provide a graphical interface displaying the probe guidance instructions. A clinician performing an examination at the patient location can read the probe guidance instructions from the UT/display 132 and maneuver the probe 110 accordingly.

The system 100 can be configured for use in various stages of ultrasound imaging. In an embodiment, the system 100 may be used for collecting ultrasound images and tracking movements of the probe 110 to form a training data set for deep learning network training. For example, the host 130 may include a memory 138, which may be any suitable storage device, such as a cache memory (e.g., a cache memory of the processing component 134), random access memory (RAM), magnetoresistive RAM (MRAM), read-only memory (ROM), programmable read-only memory (PROM), erasable programmable read only memory (EPROM), electrically erasable programmable read only memory (EEPROM), flash memory, solid state memory device, hard disk drives, solid state drives, other forms of volatile and non-volatile memory, or a combination of different types of memory. The memory 138 can be configured to store a training data set 140 for deep learning-based training.

In some embodiments, the system 100 may be used for training deep learning networks for probe positioning. For example, a deep learning network may be trained by associating probe positions and corresponding image views and a target image view. The deep learning network may be trained to predict optimal movements (e.g., rotations and/or translations) to move a probe (e.g., the probe 110) towards the target image view. The trained deep learning network can be stored in the memory 138 for subsequent use.

In some embodiments, the system 100 may be used in a clinical setting for live ultrasound examinations, where a trained deep learning network may be applied to provide automatic probe positioning guidance and the camera 150 may be used to capture images of the probe 110 for image-based tracking. The deep learning-based predicted movements along with the image-based tracking information can be used to guide a clinician in locating an optimal view for an ultrasound examination. Mechanisms for collecting training data, training a deep learning network, and applying deep learning techniques and image-based tracking techniques for automatic probe positioning guidance are described in greater detail herein.

While the system 100 is illustrated with beamforming and signal processing functions performed by the beamformer 114 and the processing component 116, respectively, at the probe 110, in some embodiments, at least some of the beamforming and/or signal processing functions may be performed at the host 130. In some other embodiments, the probe 110 may transfer the ultrasound echo signals, for example, with some gain controls and/or filtering, to the host 130 for processing. In addition, the communication interface 118 at the probe 110 may be an industry standard physical connector and/or a proprietary physical connector and the communication link 120 may include any industry standard cables, coaxial cables, and/or proprietary cables. In general, the system 100 may represent any types of ultrasound imaging system, where ultrasound imaging functionalities may be partitioned in any suitable manner across a probe (e.g., including a transducer 112), a host, and/or any intermediate processing subsystem between the probe and the host. Further, while the system 100 is illustrated with the camera 150 for tracking probe movements with respect to the patient, in some embodiments, the system 100 can include any suitable tracking device on the patient, on the probe 110, or positioned at any suitable location where the examination is being performed.

Generally, the system 100 and the probe 110, and/or other devices described herein can be utilized to examine any suitable anatomy and/or lumen of the patient body. In some instances, the probe 110 can be positioned within the anatomy and/or lumen of the patient body. In other instances, the probe 110 can be positioned outside of body to examine the anatomy and/or lumen inside of the body. For the anatomy and/or lumen may represent fluid filled or surrounded structures, both natural and man-made. For example, a probe of the present disclosure can be positioned within and/or used to examine an esophagus of the patient. In some embodiments, a probe of the present disclosure may be used to examine any number of anatomical locations and tissue types, including without limitation, organs including the liver, heart, kidneys, gall bladder, pancreas, lungs; ducts; intestines; nervous system structures including the brain, dural sac, spinal cord and peripheral nerves; the urinary tract; as well as valves within the blood, chambers or other parts of the heart, and/or other systems of the body. The anatomy and/or lumen inside of the body may be a blood vessel, as an artery or a vein of a patient's vascular system, including cardiac vasculature, peripheral vasculature, neural vasculature, renal vasculature, and/or or any other suitable lumen inside the body. In addition to natural structures, a probe of the present disclosure may be used to examine man-made structures such as, but without limitation, heart valves, stents, shunts, filters and other devices.

Figure 2:
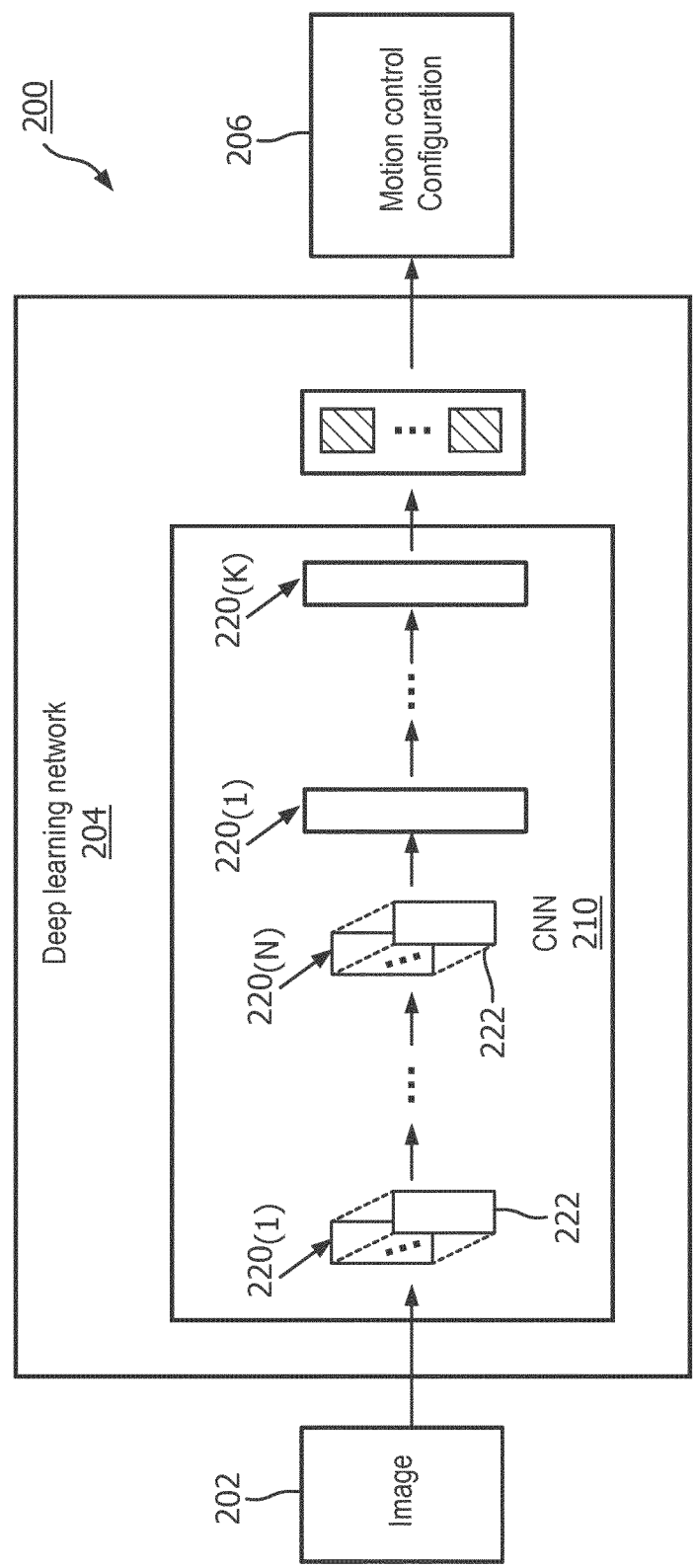
FIG. 2 is a schematic diagram illustrating a deep learning-based automatic probe positioning guidance scheme, according to aspects of the present disclosure.

FIG. 2 is a schematic diagram illustrating a deep learning-based automatic probe positioning guidance scheme 200, according to aspects of the present disclosure. The scheme can be implemented by the system 100. The scheme 200 includes a deep learning network 204. The deep learning network 204 may include one or more convolutional neural networks (CNNs) 210. The CNN 210 may be trained to provide a set of movements for moving an ultrasound imaging probe (e.g., the probe 110) to an optimal imaging position or imaging plane for capturing a particular view of a patient's anatomy (e.g., a patient's heart) based on a current imaging view.

As an example, a clinician may select a target image view and may position the probe at a first position with respect to a patient's heart. The probe may capture an image 202 (e.g., a current image view) of the patient's heart at the first position. The scheme 200 may apply the trained CNN 210 to the image 202. The CNN 210 may output a motion control configuration 206 based on the current image 202 captured at the first position. The motion control configuration 206 may include any vectorial parametrization and/or non-vectorial parametrization of a rigid-body motion. The parametrizations can be in the form of Euler angles, quaternions, matrix, exponential map, and/or angle-axis representing rotations and/or translations (e.g., including a direction and a magnitude for the translations) for moving the probe towards the target image view.

The CNN 210 may include a set of N convolutional layers 220, followed by a set of K fully connected layers 240, where N and K may be any positive integers. Each fully connected layer 240 can include M neurons, where M may be any positive integer. The values N, K and M may vary depending on the embodiments. In some instances, N may be about 8, K may be about 2, and M can be about 1000. Each convolutional layer 220 implements a non-linear transformation, which may be a composite function of operations, such as batch normalization, rectified linear units (ReLU), pooling, dropout, or convolution. Each convolutional layer may include a set of filters 222 configured to extract features from the image 202. In addition, each convolutional layer 220 may include a non-linearity function (e.g., including rectified non-linear (ReLU) operations) configured to extract rectified feature maps. The fully connected layers 240 may be non-linear and may gradually shrink the high-dimensional output of the last convolutional layer $220_{(N)}$ to produce a set of candidate motion control configurations 252 (e.g., each including a rotation and/or translation) for moving the probe towards the target image view. The CNN 210 may output a vectorial or non-vectorial parametric representation of the motion control configuration 206 that describes motion of the probe towards the target image view.

The CNN 210 can be trained using a training data set including images generated from simulated data, images acquired from a phantom in a control setting, lives images acquired during a clinical setting, or a combination thereof. The training data set further includes associations between the images and corresponding probe movements. The training of the CNN 210 extracts and learns features (e.g., clinical properties) from the images and the associating probe movements by adjusting the coefficients of the filters 222 and 232, as describe in greater detail herein.

Figure 3:
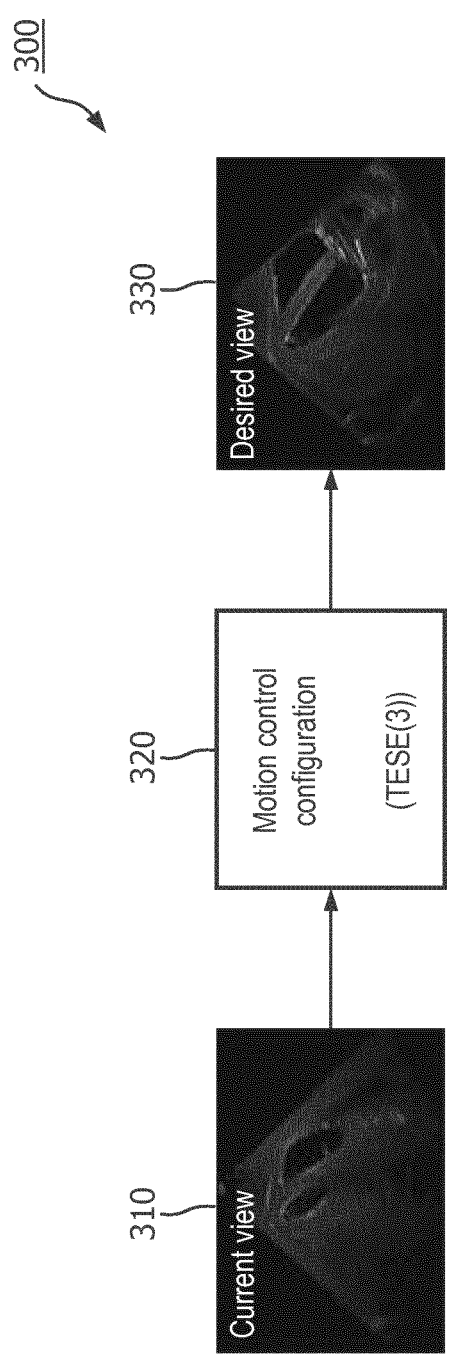
FIG. 3 illustrates a use case scenario for a deep learning-based automatic probe positioning guidance scheme, according to aspects of the present disclosure.

FIG. 3 illustrates a use case scenario 300 for the deep learning-based automatic probe positioning guidance scheme 200. In the scenario 300, a current image view 310 of a patient's heart is captured when a probe (e.g., the probe 110) is positioned at a first position with respect to the patient. The current image view 310 may correspond to the image 202 in the scheme 200. The CNN 210 is applied to the current image view 310. The CNN 210 produces a motion control configuration 320 (e.g., the motion control configuration 206). The motion control configuration 320 may be expressed as shown below:

$$T \in SE(3), \quad (1)$$

where T represents the output optimal motion control configuration 320 (e.g., a rotation and/or a translation) of a rigid body (e.g., the candidate motion control configurations 252) for moving the probe and SE(3) represents a special Euclidean group.

After obtaining the motion control configuration 320, the clinician may reposition the probe to a next position according to the motion control configuration 320. After repositioning the probe to the next position (e.g., corresponding to an optimal imaging position), a target image view 330 of the patient's heart may be captured. As can be seen, the target image view 330 provides a clear view of the heart's chambers.

While the scenario 300 illustrates that the motion control configuration 320 leads the probe to an optimal imaging position for capturing the target imaging view in a single try or single application of the CNN 210, in some embodiments, the CNN 210 may be re-applied to a next captured image view. In other words, a clinician may be required to reposition the probe multiple times to reach the optimal imaging position based on multiple applications of the CNN 210.

The imaged-based motion prediction with deep learning can provide several advantages. For example, the motion prediction performance is independent from anatomical differences (e.g., patient size and/or heart location) due to the rich features extracted during the end-to-end learning or training of the CNN 210. However, the motion prediction performance can be impacted by input images with poor quality, for example, due to poor acoustic coupling, poor acoustic window positioning (e.g., rib shadowing effects in cardiac examinations), and/or sub-optimal breathing state. Accordingly, the present disclosure provides techniques to filter out image data that are irrelevant to a particular examination or image data with a poor quality before applying a deep learning network for motion prediction.

Figure 4:
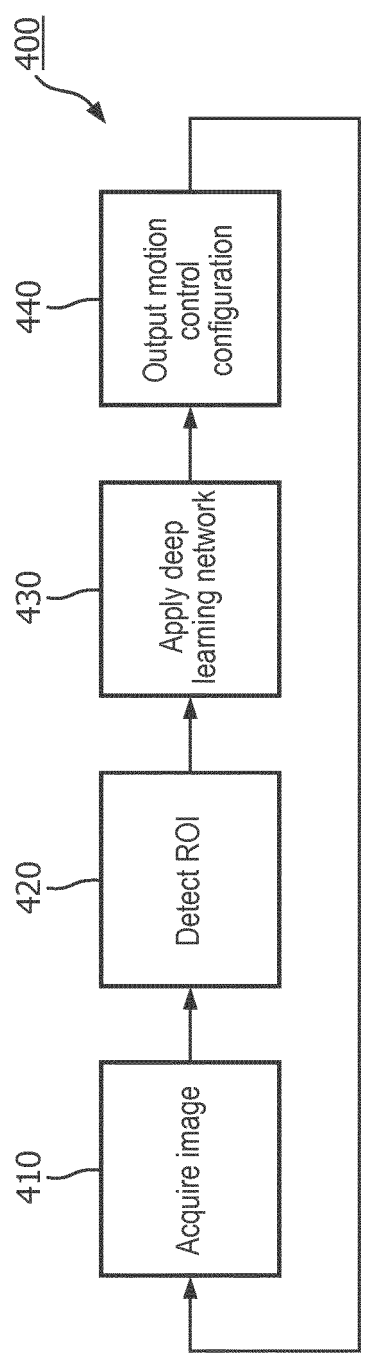
FIG. 4 is a flow diagram of an automatic probe positioning guidance method, according to aspects of the present disclosure.
Figure 5:
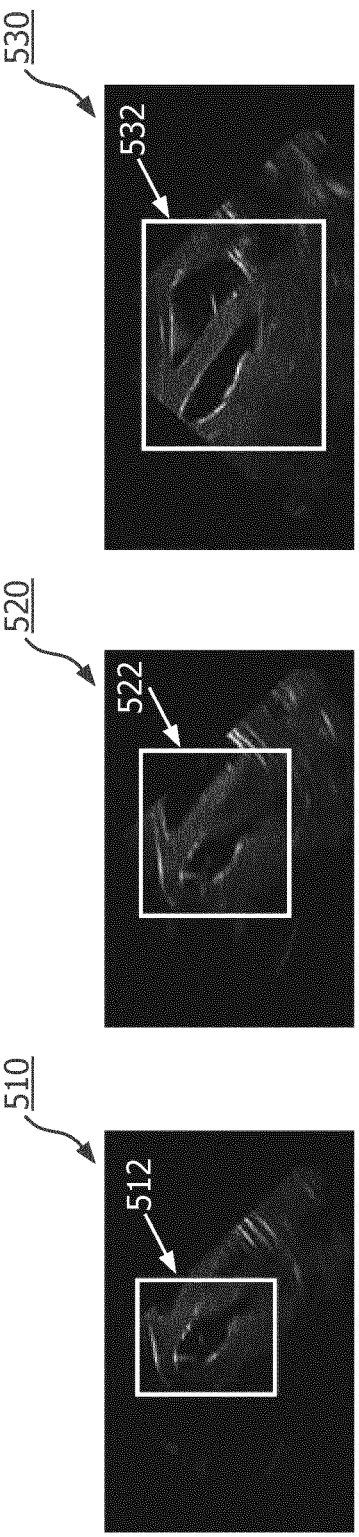
FIG. 5 illustrates ultrasound images acquired from an automatic probe positioning guidance method, according to aspects of the present disclosure.

FIG. 4 is a flow diagram of an automatic probe positioning guidance method 400, according to aspects of the present disclosure. Steps of the method 400 can be carried out using the system 100, for example, executed by the processing component 134. As illustrated, the method 400 includes a number of enumerated steps, but embodiments of the method 400 may include additional steps before, after, and in between the enumerated steps. In some embodiments, one or more of the enumerated steps may be omitted or performed in a different order. The method 400 may employ similar mechanism as in the scheme 200 described with respect to FIG. 2. The method 400 additionally detects a region of interest (ROI) (e.g., clinical relevant features) from an input image and applies a deep learning network to the ROI for motion prediction. FIG. 5 illustrates ultrasound images 510, 520, and 530 acquired from the automatic probe positioning guidance method 400, according to aspects of the present disclosure. The method 400 is described below with reference to FIG. 5.

At step 410, the method 400 includes acquiring an image (e.g., the image 202 and the current image view 310) of a patient's anatomy. For example, a clinician may position a probe (e.g., the probe 110) at a first position close to the patient's anatomy that is being examined. As an example, the clinician may perform a cardiac examination on the patient and acquire an image 510 of the patient's heart.

At step 420, the method 400 includes detecting a ROI 512 from the image 510. The ROI 512 includes a region of the image 510 corresponding to the patient's heart.

At step 430, the method 400 includes applying a deep learning network (e.g., the deep learning network 204) to the ROI 512 of the image 510. The deep learning network produces a motion control configuration (e.g., the motion control configurations 206 and 320) for positioning the probe based on the ROI 512 in the image 510.

At step 440, the method 400 includes outputting the motion control configuration to a display (e.g., the UT/display 132), for example, in the form of a graphical interface indicating a rotation and/or a translation of the probe. Thus, the clinician may reposition the probe following the displayed instructions.

The method 400 may repeat the steps 410-440 until an optimal imaging view is captured. For example, after a first iteration of the method 400, an image 520 is captured. The method 400 can be repeated to detect an ROI 522 from the image 520 and applies the deep learning network to the ROI 522. After a second iteration, an image 530 is captured. Again, the method 400 can be repeated to detect an ROI 532 from the image 530 and applies the deep learning network to the ROI 532. As can be observed, after each iteration, a better imaging view of the heart chambers is captured.

The limiting of the deep learning network to operate on the ROIs 512, 522, and 532 for motion predictions can provide several advantages. For example, the computational load can be reduced, the size of the deep learning network can be reduced, and/or the frame rate can be increased. The reduced complexity can enable the implementation of the deep learning-based motion prediction on a lower-cost, lower-performance, and/or smaller-sized processing component.

In an embodiment, the ROI detection in the step 420 can be implemented via a prediction network similar to the deep learning network 204. In another embodiment, a single deep learning network can be trained to provide the RIO detection and the motion prediction.

Figure 6:
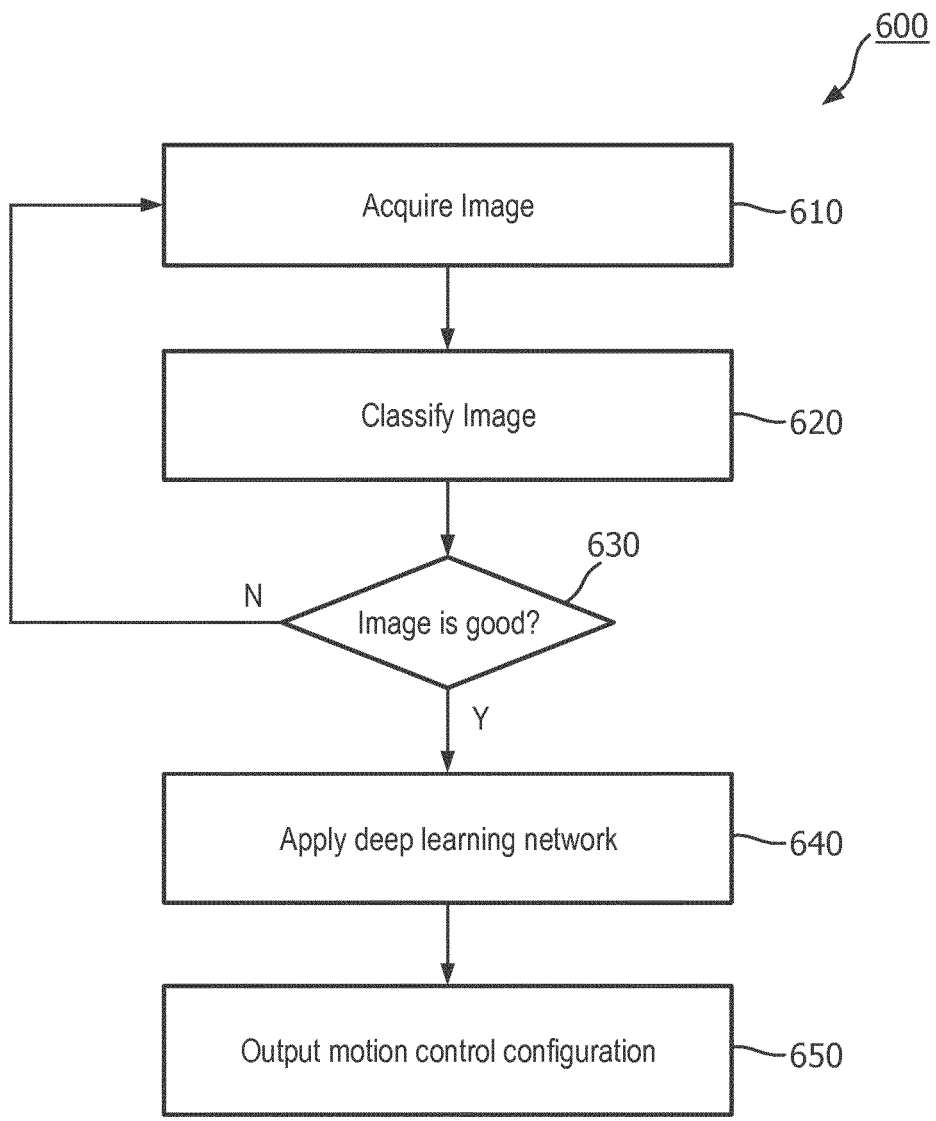
FIG. 6 is a flow diagram of an automatic probe positioning guidance method, according to aspects of the present disclosure.

FIG. 6 is a flow diagram of an automatic probe positioning guidance method 600, according to aspects of the present disclosure. Steps of the method 600 can be carried out using the system 100, for example, executed by the processing component 134. As illustrated, the method 600 includes a number of enumerated steps, but embodiments of the method 600 may include additional steps before, after, and in between the enumerated steps. In some embodiments, one or more of the enumerated steps may be omitted or performed in a different order. The method 600 may employ similar mechanism as in the scheme 200 described with respect to FIG. 2. The method 600 additionally filters out input images with a poor quality before applying a deep learning network for motion prediction.

At step 610, the method 600 includes acquiring an image (e.g., the images 202. 510, 520, and 530 and the current image view 310) of a patient's anatomy. For example, a clinician may position a probe (e.g., the probe 110) at a first position close to the patient's anatomy that is being examined.

At step 620, the method 600 includes classifying the image, for example, based on an image quality measure. In some instances, a softmax function may be applied for the classification.

At step 630, the method 600 determines whether the image has a good quality.

When the image has a good quality, the method 600 proceeds to step 640. At step 640, the 600 includes applying a deep learning network (e.g., the deep learning network 204) to the image. The deep learning network produces a motion control configuration (e.g., the motion control configurations 206 and 320) for positioning the probe towards an optimal imaging view.

At step 650, the method 600 includes outputting the motion control configuration to a display (e.g., the UT/display 132), for example, in the form of a graphical interface indicating a rotation and/or a translation of the probe. Thus, the clinician may reposition the probe following the displayed instructions.

Returning to the step 620, when the image has a poor quality, the method 600 discards the image and returns to the step 610 to acquire a next image.

In an embodiment, the classification in the step 620 can be implemented via a prediction network similar to the deep learning network 204. In another embodiment, a single deep learning network can be trained to provide the image classification and the motion prediction.

In some embodiments, the method 600 may be used in conjunction with the method 400. In one example, the ROI detection, the image classification, and the motion prediction can be implemented via one or more prediction networks in any suitable combinations. In another example, the ROI detection and/or the image classification can be performed by a clinician prior to applying the deep learning network.

The accuracy of the imaged-based motion prediction can be susceptible to image quality. For example, it may be difficult to obtain high-quality images for certain patients that are difficult to work with (e.g., due to obesity and/or small intercostal space) for certain imaging positions. Accordingly, the present disclosure provides techniques to provide assistances to the imaged-based motion prediction by combining AR markers with the imaged-based motion prediction.

Figure 7:
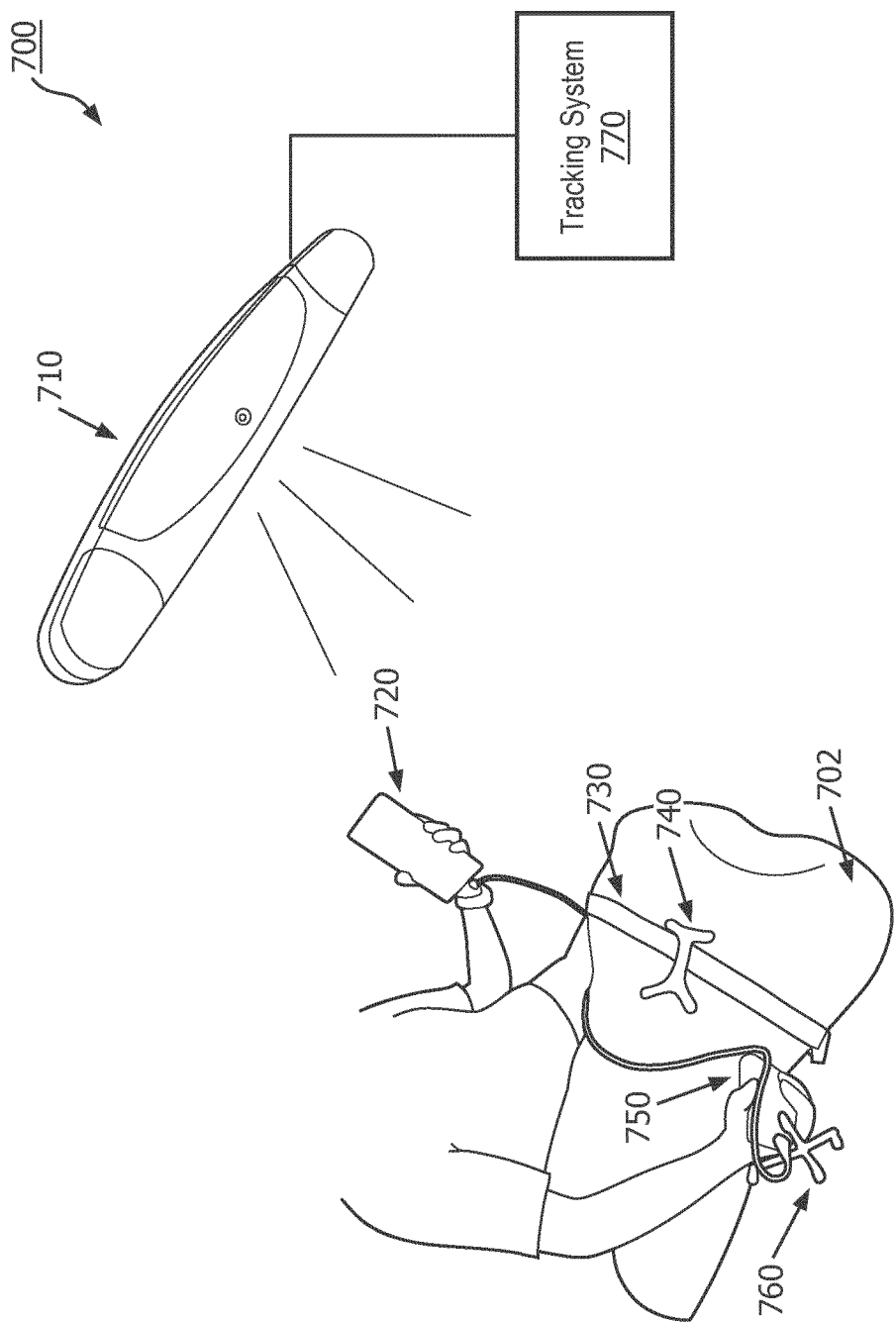
FIG. 7 is a schematic diagram illustrating a training data acquisition scheme, according to aspects of the present disclosure.

FIG. 7 is a schematic diagram illustrating a training data acquisition scheme 700, according to aspects of the present disclosure. The scheme 700 may be implemented offline to collect training data (e.g., the training data set 140) for training a deep learning network (e.g., the deep learning network 204) to provide motion prediction in automatic probe guidance. The scheme 700 collects training data using a phantom 702. The scheme 700 may be alternatively configured to collect training data from clinical sonographic examinations.

As an example, the scheme 700 collects training data for a cardiac examination. A patient tracker 740 is positioned on the phantom 702 marking the location of the phantom 702's heart. The patient tracker 740 is strapped to the phantom 702 by a belt strap 730. The scheme 700 acquires images of the phantom 702's heart using a probe 750. The probe 750 may be similar to the probe 110. The probe 750 is coupled to a mobile device 720 (e.g., a tablet or smart phone) where the acquired images can be transferred to the mobile device 720 to create the training data set. The mobile device 720 may be similar to the host 130. A probe tracker 760 is attached to the probe 750. The scheme 700 further utilizes an optical capturing device 710 or a camera (e.g., the camera 150) to track the movements of the probe 750 with reference to the phantom 702's heart via the probe tracker 760 and the patient tracker 740, respectively. The optical capturing device 710 may be communicatively coupled to a tracking system 770. The scheme 700 may alternatively or additionally employ a position measurement system, such as an electromagnetic tracking system, to track the movements of the probe 750.

The mobile device 720 may collect images of the phantom 702's heart with the probe 750 positioned at various imaging positions. The tracking system 770 may include a computing and processing component (e.g., the host 130) configured to record movements (e.g., rotations and/or translations) of the probe tracker 760 with respect to the patient tracker 740. The mobile device 720 can timestamp the collected images. Similarly, the tracking system 770 can timestamp the recoded movements. The scheme 700 can synchronize and associate the collected images with corresponding movements of the probe based on the timestamps of the images and the timestamps of the movements. After the synchronization, the scheme 700 can create a training data set by associating the images with corresponding movements.

While the scheme 700 uses the patient tracker 740 and the probe tracker 760 to assist the tracking of the probe 750's movements with respect to the phantom 702's heart, the use of the patient tracker 740 and/or the probe tracker 760 can be optional. In addition, the scheme 700 can be applied to collect images of any suitable anatomy (e.g., lungs, kidney, liver, and/or any organs, tissues, vessels) and track movements of the probe to generate a training data set.

After collecting the training data set, the training data set can be fed into the deep learning network 204, for example, using forward propagation. The input to the training of deep learning network 204 is a 2-tuple (e.g., including an image and a pose or motion control configuration). The coefficients for the filters 222 and 232 may be adjusted, for example, by using backward propagation or backpropagation to minimize the output error of the network 204.

Figure 8:
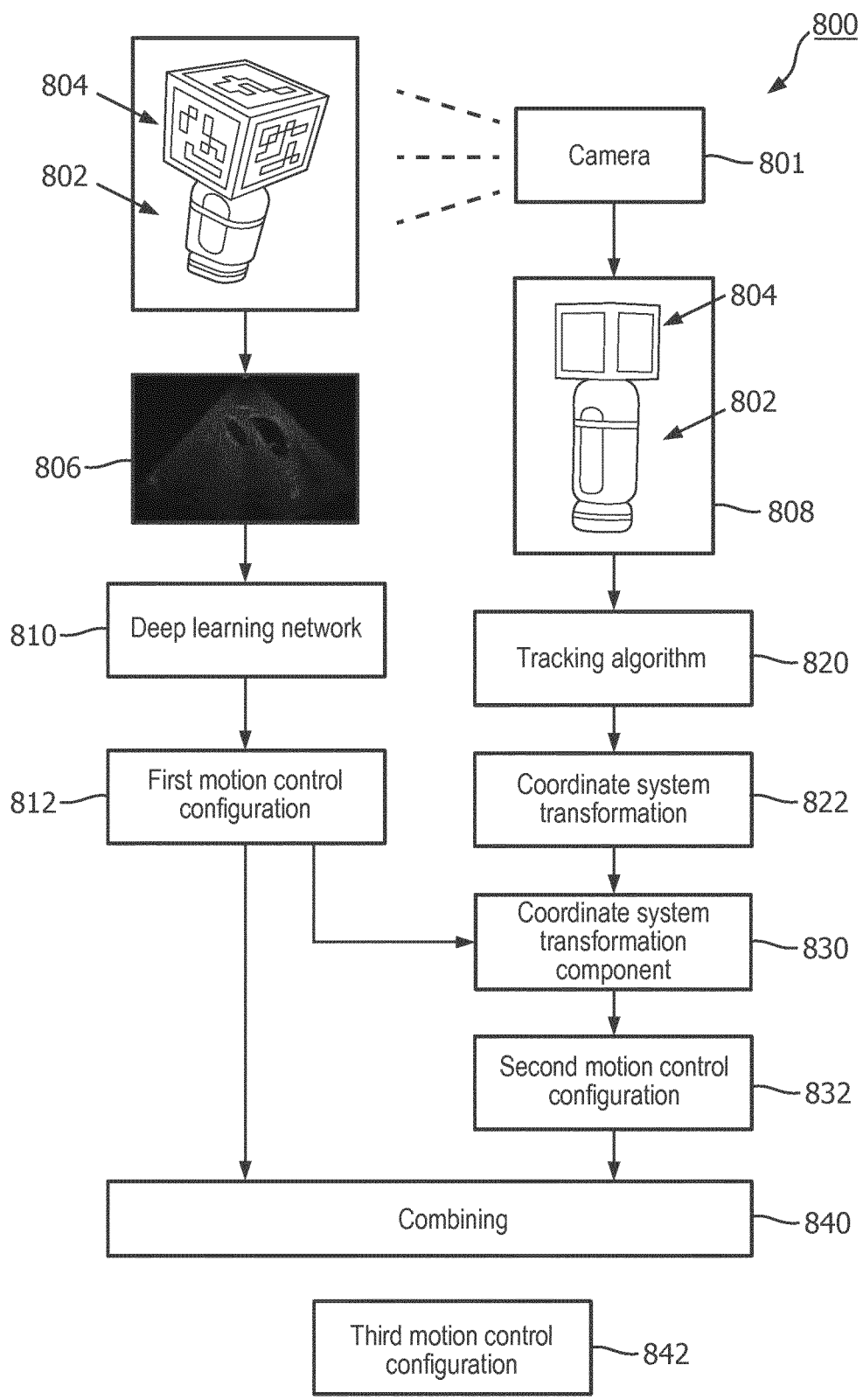
FIG. 8 is a schematic diagram illustrating a hybrid automatic probe positioning guidance scheme implementing imaged-based motion prediction with an augmented reality (AR) marker and camera tracking, according to aspects of the present disclosure.

FIG. 8 is a schematic diagram illustrating a hybrid automatic probe positioning guidance scheme 800 implementing imaged-based motion prediction with an AR markers and camera tracking, according to aspects of the present disclosure. The scheme 800 can be implemented by the system 100. The scheme 800 employs a probe 802 similar to the probes 110 and 750 to acquire images (e.g., the images 202, 510, 520, and 530) of a patient's anatomy (e.g., heart, lungs, liver, kidney, and/or any organ, vessels, tissues or structures). An AR marker 804 is coupled to the probe 802. The scheme 800 employs a camera 801 similar to the optical capturing device 710 and the camera 150 to simultaneously capture camera images of positions and movements of the probe 802 and the probe marker 804 in real-time.

In the scheme 800, a clinician may position the probe 802 at a first position to capture an image 806 of the patient's anatomy under examination. At the same time, the camera 801 captures camera images 808 of the probe 802 (e.g., positions and/or movements) in real-time.

The image 806 is input to a deep learning network 810 similar to the deep learning network 204. The deep learning network 810 produces a first motion control configuration 812 for repositioning the probe 802 towards a desired or target imaging position. The motion control configuration 812 may include rotations and/or translations with respect to a first coordinate system (e.g., the coordinate system of outputs by the deep learning network 810). The first coordinate system may be defined during the training of the deep learning network 810. The first coordinate system may be a local coordinate system of the heart defined by features identified on images (e.g. including apical four-chamber view) acquired during the training.

A tracking algorithm 820 determines a coordinate system transformation 822 between a coordinate system of the AR marker 804 and a coordinate system of the camera 801 (e.g., optical tracking) based on the live camera images 808. The coordinate system of the camera 801 is referred to as a second coordinate system. For example, the tracking algorithm 820 may apply image processing techniques to identify the AR marker 804 and track the movements of the AR marker 804 corresponding to the movements of the probe 802. The AR marker 804 can be imprinted with certain visual patterns that can be easily recognized or identified by image processing algorithms.

In an embodiment, the AR marker 804 may be calibrated against the ultrasound probe 802 to obtain a transformation between the probe 802 and the AR marker coordinate system. The tracking algorithm 820 tracks positional information associated with the probe 802 with respect to the patient's anatomy in the second coordinate system. The coordinate system transformation 822 may include rotations and/or translations with respect to the second coordinate system.

The first coordinate system and the second coordinate system may be different. The first motion control configuration 812 and the coordinate system transformation 822 are input to a coordinate system transformation component 830. The coordinate system transformation component 830 applies the coordinate system transformation 822 to the first motion control configuration 812 to produce a transformed motion control configuration, which is referred to as a second motion control configuration 832, with respect to the first coordinate system. A coordinate system transformation may include rotations and/or translations of a coordinate system such that the coordinate system is in alignment to a reference coordinate system.

In an embodiment, the coordinate system transformation component 830 may apply the transformation as shown below:

$$\text{camera}T_{DL} = \text{camera}T_{marker} \times \text{marker}T_{probe} \times \text{probe}T_{DL}, \quad (2)$$

where $\text{probe}T_{DL}$ represents a coordinate system transformation from a local anatomically-defined coordinate system (e.g., the first coordinate system of the deep learning network 810) to the probe 802. The local anatomy-based coordinate system can be arbitrarily chosen in the training process. The $\text{marker}T_{probe}$ represents a coordinate system transformation from the probe 802 to the AR marker 804. The $\text{camera}T_{marker}$ represents a coordinate system transformation (e.g., the coordinate system transformation 822) from the AR marker 804 to the camera 801. The $\text{camera}T_{DL}$ represents the coordinate system transformation performed by the coordinate system transformation component 830, i.e. a transformation between the first motion control configuration 812 outputs by the deep learning network 810 (e.g. with respect to the local coordinate of the anatomy of interest, such as the patient's heart) and camera-based tracking algorithm 820. Thus, the transformation $\text{camera}T_{DL}$ represents a coordinate system registration between the deep learning network 810 and the camera 801.

In an embodiment, the transformation $\text{marker}T_{probe}$ can be fixed and can be calibrated during the production of the probe 802 with the coupled AR marker 804. In another embodiment, the AR marker 804 can be attached to the probe 801 during operations of the system (e.g., when implementing the scheme 800) via a mounting mechanism that can provide reproducible positioning. In some other embodiments, the AR marker 804 can be calibrated to the ultrasound probe 802 and an image (e.g., a camera image) using an external ultrasound phantom with known engraved internal landmarks.

In an embodiment, the transformation $\text{camera}T_{DL}$ can be determined at the beginning of the examination and updated during the examination. It should be noted that Equation (2) assumes that the camera 801 is located at a fixed location with respect to the patient during the sonographic examination.

In an embodiment, the camera 801 may be moving during the examination. Thus, the coordinate system transformation 822 is required to account for the moving the camera 801 at different locations. In such an embodiment, the coordinate system transformation component 830 can apply the transformation as shown below:

$$\text{patient}T_{DL} = \text{patient}T_{cam} \times \text{camera}T_{marker} \times \text{marker}T_{probe} \times \text{probe}T_{DL}, \quad (3)$$

where $\text{patient}T_{camera}$ represents a coordinate transformation from the camera 801 to the patient under the examination. Patient coordinate system can be defined by a patient marker similar to the patient marker 760.

In general, the coordinate system transformation component 830 applies the transformation to align the first coordinate system (e.g., used to represent the first motion control configuration 812) and the second coordinate system (e.g., of the camera 801) to a common reference coordinate system.

After applying the transformation, a combining function 840 may be applied to combine the first motion control configuration 812 with the second motion control configuration 832 to produce a third motion control configuration 842. In an embodiment, the combining function 840 averages the first motion control configuration 812 with the second motion control configuration 832. In an embodiment, the combining function 840 combines the first motion control configuration 812 and the second motion control configuration 832 with certain weightings. In an example, the first motion control configuration 812 can be compared to the second motion control configuration 832 to validate the accuracy of the first motion control configuration 812 predicted by the deep learning network 810, where the combining function 840 may be dependent on the comparison. For example, if the comparison satisfies a certain threshold, then the first motion control configuration 812 can be averaged or replaced with the second motion control configuration 832. The third motion control configuration 842 can be output to a graphical interface (e.g., the UT/display 132) to provide probe positioning guidance to the clinician as described in greater detail herein below.

The clinician may reposition the probe 802 according to the probe positioning guidance instruction. The clinician may repeat the scheme 800 to reposition the probe 802 until reaching an optimal imaging positions for the examination.

In some embodiments, the scheme 800 may store the probe repositioning sequence used for the examination based on the tracking coordinate system (e.g., the second coordinate system) in case the clinician wants to recall the probe repositioning sequence used for the examination.

In some embodiments, the scheme 800 may be used in conjunction with the methods 400 and/or 600. For example, the deep learning network 810 may include the ROI detection shown in the method 400 and/or the image classification as shown in the method 600 in addition to probe motion prediction.

In an embodiment, a sonographer may find an apical-four chamber view using imaged-based guidance (e.g., the deep learning-based motion prediction). After finding the apical-four chamber view, a registration between the deep learning network 810 and the camera is performed, for example, as shown in Equation (2) or Equation (3). After the registration, the camera can be kept the same position (e.g., a fixed position). Otherwise, the registration may be repeated. The motion predicted by the deep learning network 810 can be combined with the tracking information obtained from the camera 801. The combining may include applying an averaging function to the predicted motion and the tracking information. Alternatively, the combining may use the tracking as a validation (e.g., a sanity check) for the predicted motion. In some instances, reference positions may be kept in the tracker coordinate system (e.g., the second coordinate system) in case a user wants to recall the positioning of the probe 802.

Figure 9:
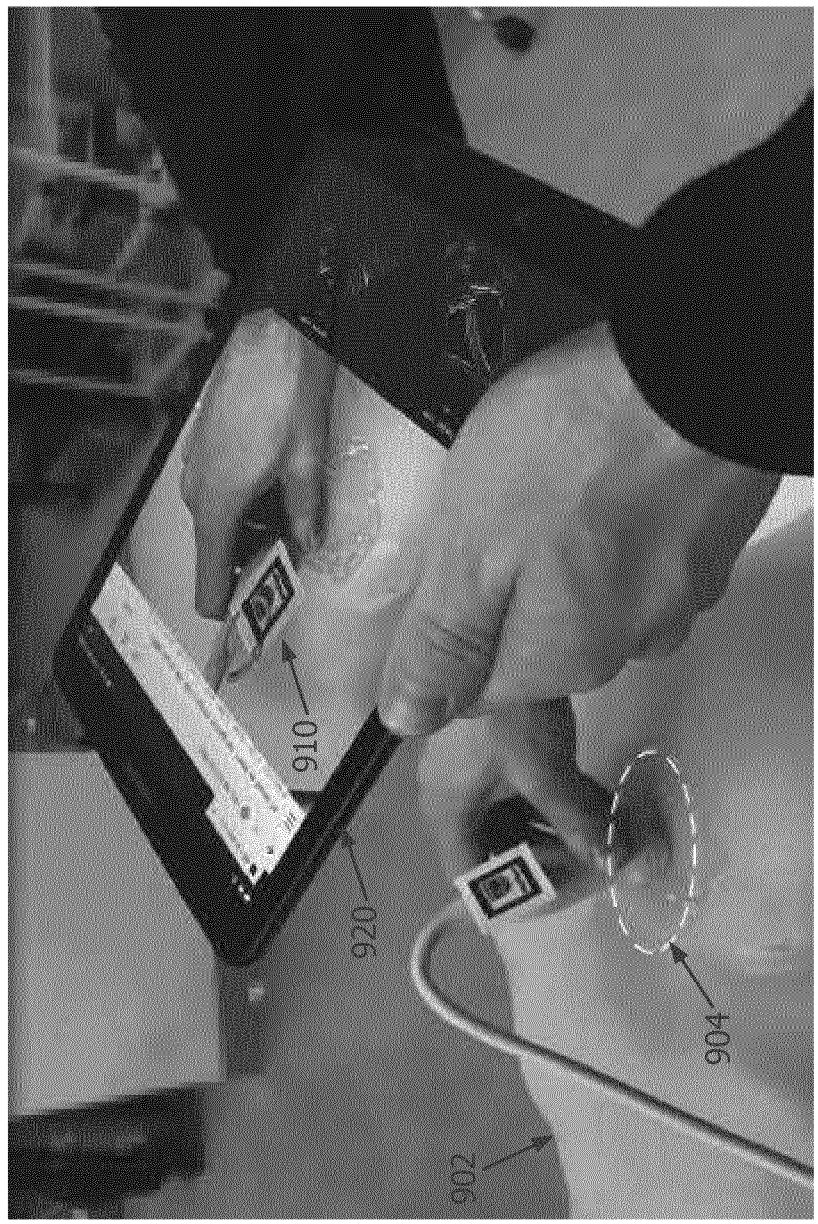
FIG. 9 illustrates a use case scenario for hybrid probe positioning guidance, according to aspects of the present disclosure.

FIG. 9 illustrates a use case scenario 900 for hybrid probe positioning guidance, according to aspects of the present disclosure. The scenario 900 may corresponds to a scenario in an ultrasound examination using the scheme 800. In the scenario 900, a clinician performs an ultrasound examination on a patient 902 using a probe 910 (e.g., the probe 802). The clinician may use a mobile device 920 equipped with a back-facing camera (e.g., the cameras 150 and 801 and the optical capturing device 710) to capture camera images of the probe 910 and the patient 902's anatomy under examination as shown on the display of the mobile device 920. As an example, the probe 910 is placed near a location 904 of the patient 902's heart for a cardiac ultrasound examination. The mobile device 920 can implement the scheme 800 described above with respect to FIG. 8. For example, the mobile device 920 can receive images acquired by the probe 910 and apply a deep learning network (e.g., the deep learning networks 204 and 810) to predict a first motion control configuration (e.g., the first motion control configuration 812) for maneuvering the probe 910 to an optimal imaging position. The mobile device 920 can implement the tracking algorithm 820 to determine a coordinate system transformation (e.g., the coordinate system transformation 822) and apply the coordinate system transformation to the deep learning predicted motion control configuration. The mobile device 920 can display probe guidance instructions using a graphical representation, as described in greater detail below.

Figure 10:
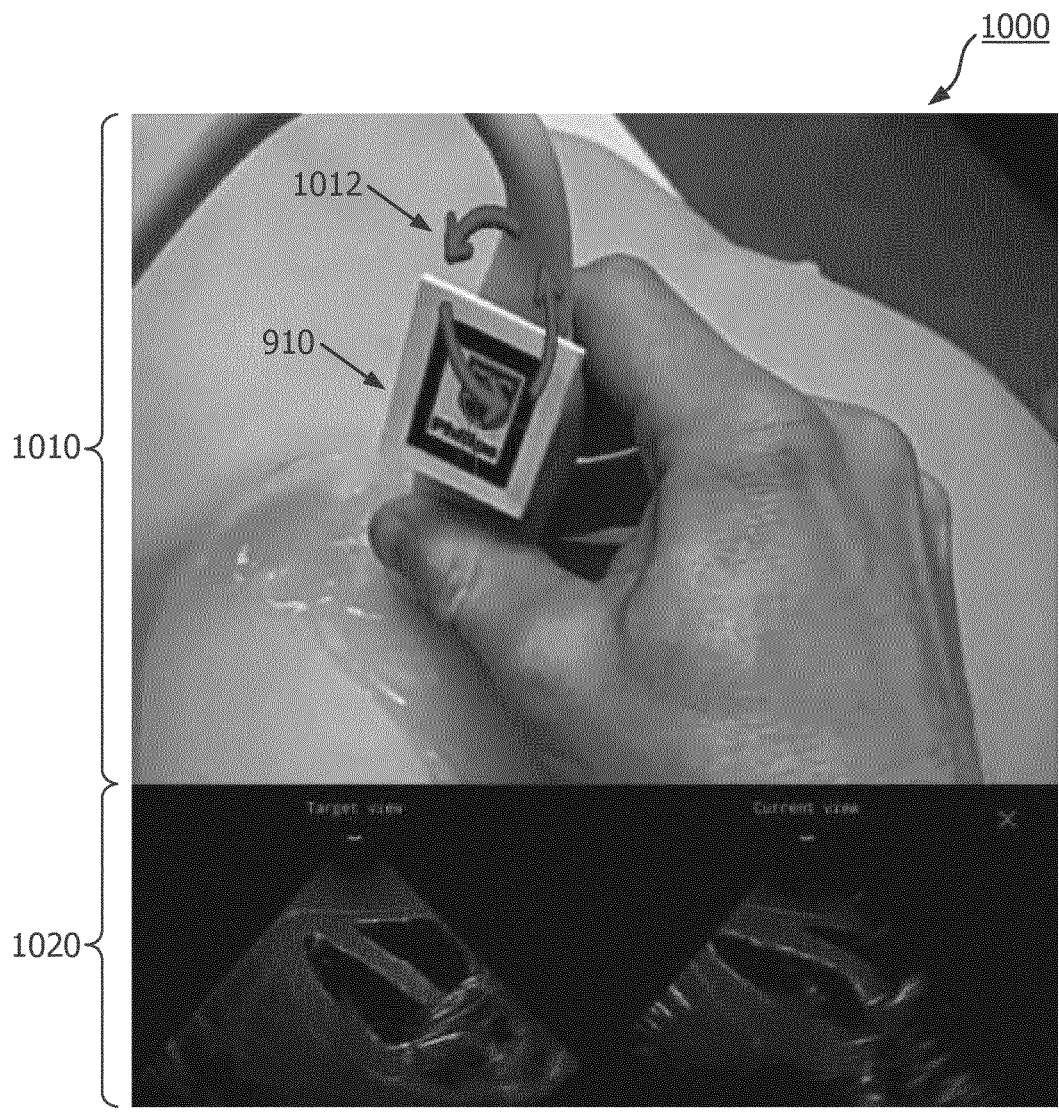
FIG. 10 illustrates a display view in an ultrasound system that provides automatic probe positioning guidance, according to aspects of the present disclosure.

FIG. 10 illustrates a display view 1000 in an imaging system that provides automatic probe positioning guidance, according to aspects of the present disclosure. The display view 1000 may correspond to a display view on the mobile device 920 implementing the scheme 800. The display view 1000 includes a camera image 1010 (e.g., the camera images 808) of the probe 910 with a probe guidance instruction (e.g., a rotation 1012) overlaid on top of the image of the probe 910. The rotation 1012 may correspond to the third motion control configuration 842. The display view 1000 further includes ultrasound images 1020 acquired by the probe 910, for example, at a first imaging position and a subsequent imaging position. Thus, a clinician may maneuver the probe 910 based on the instructions (e.g., the rotation 1012) on the display view 1000 and simultaneously observe the ultrasound images 1020 as the probe 910 changes from one position to another position. While the display view 1000 is illustrated using the mobile device 920, similar display view can be provided on the UT/display 132 in the system 100 or any display in an ultrasound imaging system.

Figure 11A:
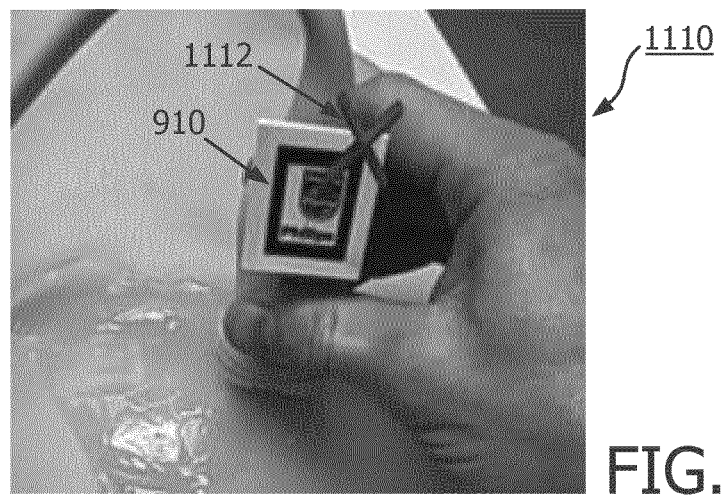
FIG. 11A illustrates a display view in an imaging system that provides automatic probe positioning guidance, according to aspects of the present disclosure.

FIGS. 11A-11E illustrate several examples of probe positioning guidance scenarios provided by the scheme 800. FIG. 11A illustrates a display view 1110 in an imaging system (e.g., the system 100) that provides automatic probe positioning guidance, according to aspects of the present disclosure. The display view 1110 may correspond to a display view on the screen of the mobile device 920. The display view 1110 is similar to the display view 1000, but illustrates an indication of an incorrect probe position as shown by the cross 1112. The cross 1112 serves as a warning that the image quality might not be sufficient to provide image-based guidance. Poor image quality can be due to inappropriate acoustic windows, poor acoustic coupling, and anatomy related (small intercostal space or certain anatomical abnormalities).

Figure 11B:
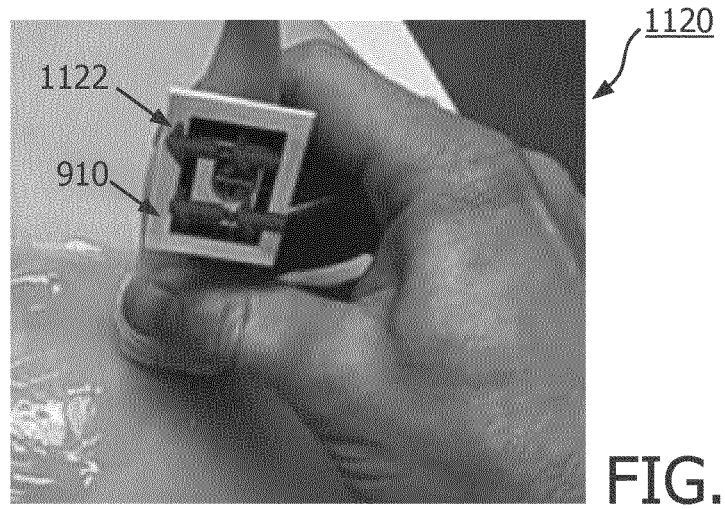
FIG. 11B illustrates a display view in an imaging system that provides automatic probe positioning guidance, according to aspects of the present disclosure.

FIG. 11B illustrates a display view 1120 in an imaging system (e.g., the system 100) that provides automatic probe positioning guidance, according to aspects of the present disclosure. The display view 1120 may correspond to a display view on the screen of the mobile device 920. The display view 1120 is similar to the display view 1000, but illustrates a translation instruction to move the probe 910 sideways to the left as shown by the arrows 1122.

Figure 11C:
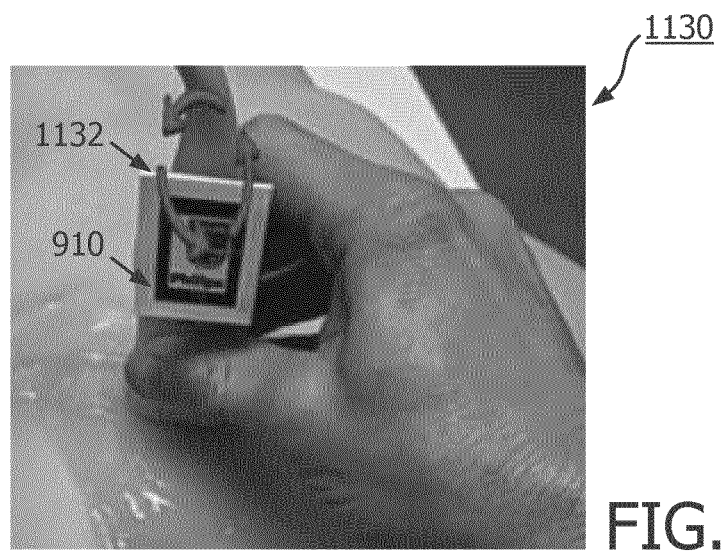
FIG. 11C illustrates a display view in an imaging system that provides automatic probe positioning guidance, according to aspects of the present disclosure.

FIG. 11C illustrates a display view 1130 in an imaging system (e.g., the system 100) that provides automatic probe positioning guidance, according to aspects of the present disclosure. The display view 1130 may correspond to a display view on the screen of the mobile device 920. The display view 1130 is similar to the display view 1000, but illustrates a rotation instruction to rotate the probe 910 in an anti-clockwise direction as shown by the rotation symbol 1132.

Figure 11D:
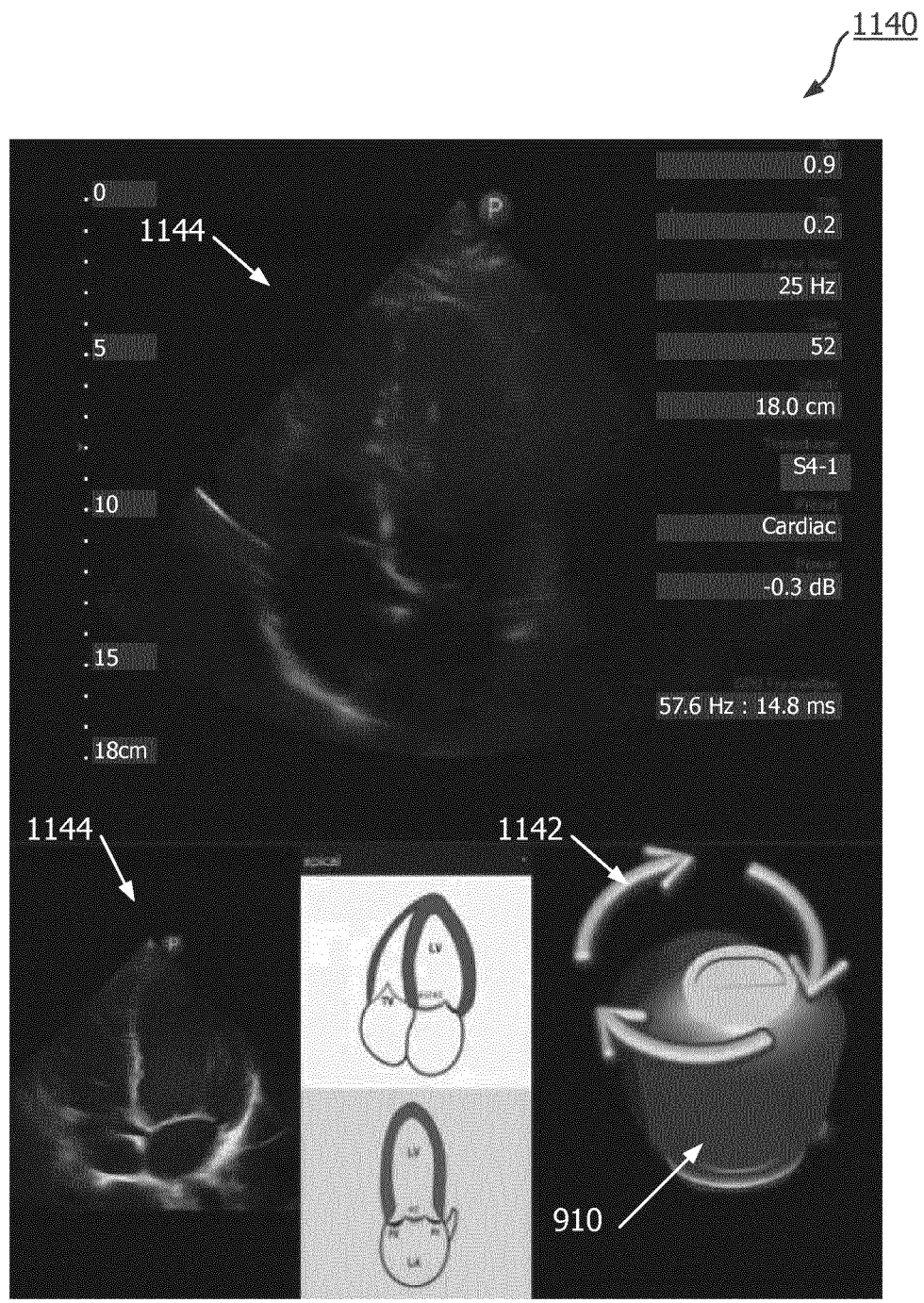
FIG. 11D illustrates a display view in an imaging system that provides automatic probe positioning guidance, according to aspects of the present disclosure.

FIG. 11D illustrates a display view 1140 in an imaging system (e.g., the system 100) that provides automatic probe positioning guidance, according to aspects of the present disclosure. The display view 1140 may correspond to a display view on the screen of the mobile device 920. The display view 1140 is similar to the display view 1000, but provides a different GUI view. The display view 1140 illustrates a rotation instruction to rotate the probe 910 in an anti-clockwise direction as shown by the rotation symbol 1142. The display view 1140 includes ultrasound images 1144 captured by the probe 910.

Figure 11E:
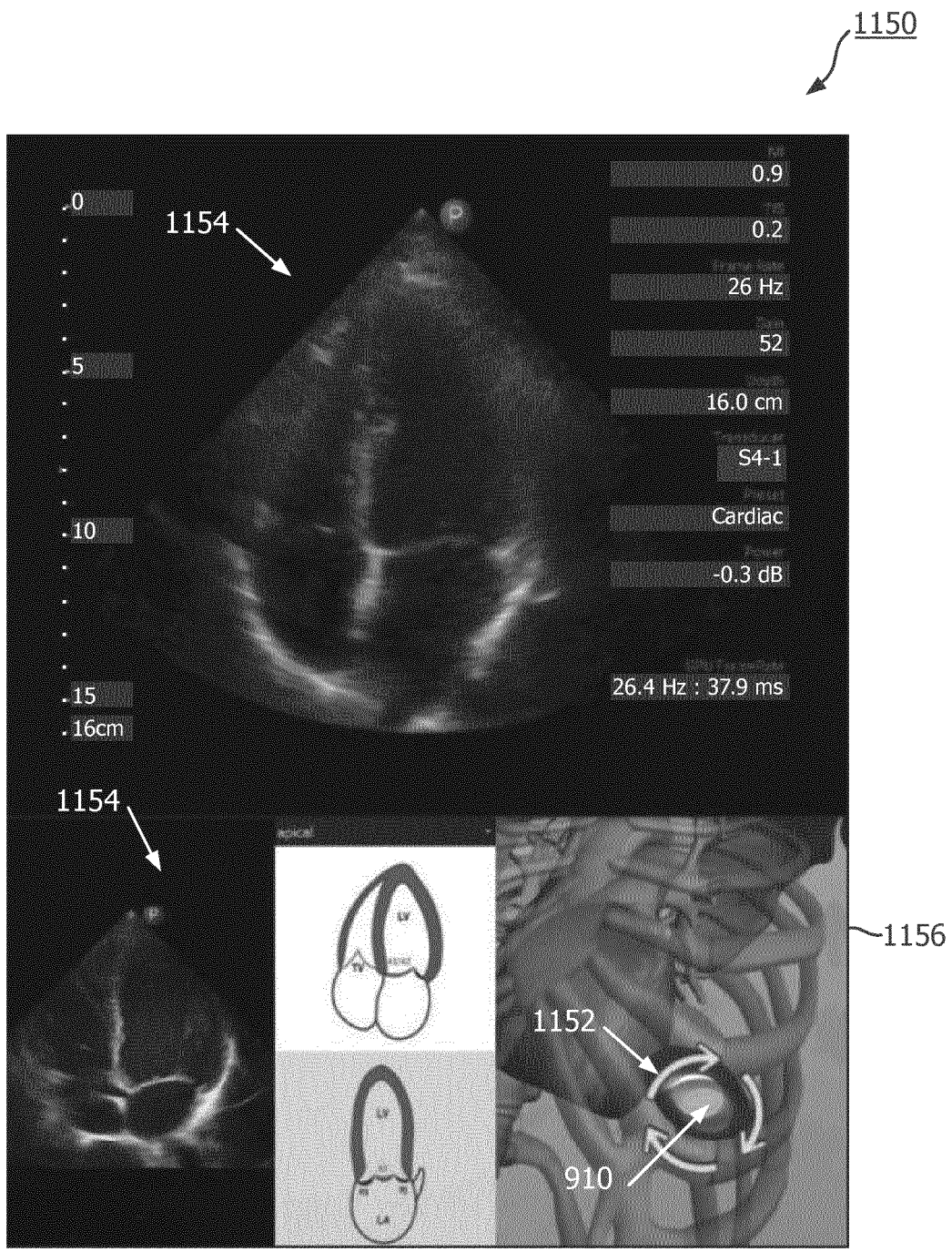
FIG. 11E illustrates a display view in an imaging system that provides automatic probe positioning guidance, according to aspects of the present disclosure.

FIG. 11E illustrates a display view 1150 in an imaging system (e.g., the system 100) that provides automatic probe positioning guidance, according to aspects of the present disclosure. The display view 1150 may correspond to a display view on the screen of the mobile device 920. The display view 1150 is similar to the display view 1140. For example, the display view 1150 illustrates a rotation instruction to rotate the probe 910 in an anti-clockwise direction as shown by the rotation symbol 1152 along with ultrasound images 1154 captured by the probe 910. However, the display view 1150 additionally includes an illustration of the position of the probe 910 with respect to the anatomy (e.g., the patient's heart) under the examination by overlaying the probe 910 on top of a phantom image 1156 representing the anatomy under the examination. When utilizing the GUI as shown in the display view 1140 and 1150, the use of AR marker (e.g., the marker 804) may not be required because guidance information is displayed directly on the screen of the mobile device 920.

Figure 12:
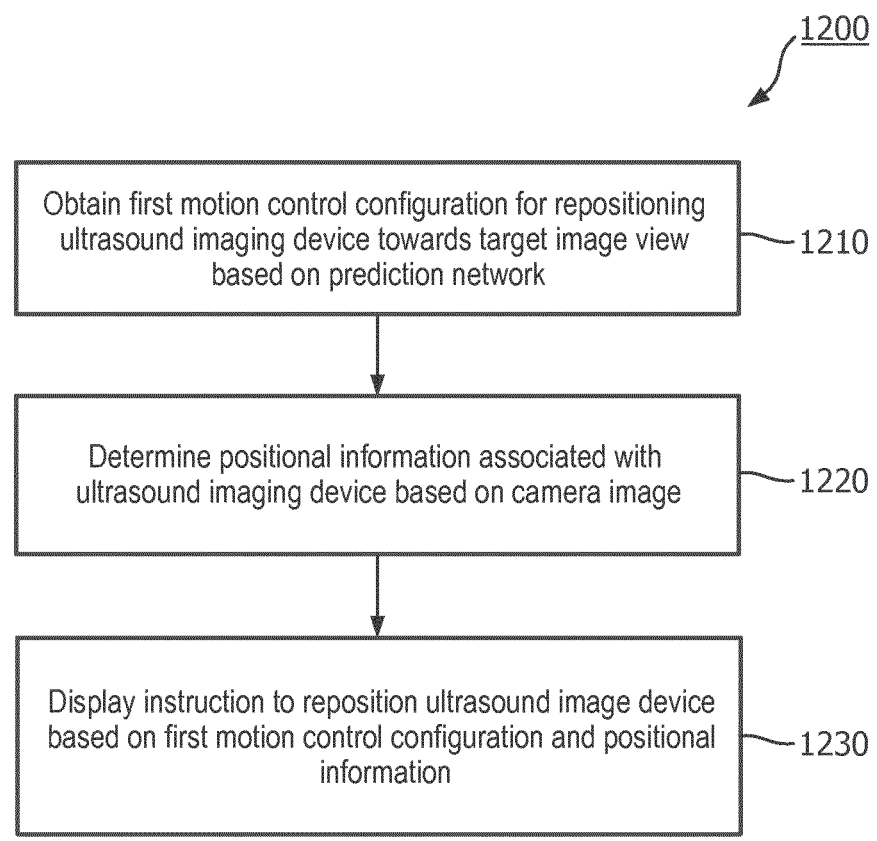
FIG. 12 is a flow diagram of a hybrid automatic probe positioning guidance method, according to aspects of the present disclosure.

FIG. 12 is a flow diagram of a hybrid automatic probe positioning guidance method, according to aspects of the present disclosure. Steps of the method 1200 can be executed by a computing device (e.g., a processor, processing circuit, and/or other suitable component) of an ultrasound imaging probe, such as the probes 110, 750, 802, and 910, or a host, such as the host 130 and the mobile device 920. The method 1200 may employ similar mechanisms as in the methods 400 and 600, the scheme 800, the scenario 900, and the display view 1000, 1110, 1120, and 1130 described with respect to FIGS. 4, 6, 8, 9, 10, 11A, 11B, and 11C, respectively. As illustrated, the method 1200 includes a number of enumerated steps, but embodiments of the method 1200 may include additional steps before, after, and in between the enumerated steps. In some embodiments, one or more of the enumerated steps may be omitted or performed in a different order.

At step 1210, the method 1200 includes obtaining a first motion control configuration (e.g., the first motion control configuration 812) for repositioning an ultrasound imaging device (e.g., the probes 110, 750, 802, and 910) positioned from a first position towards a target image view of a subject's anatomy (e.g., the object 105 or the patient's heart location 904). The first motion control configuration is determined based on a first predictive network (e.g., the deep learning network 204 and the 810).

At step 1220, the method 1200 includes determining positional information associated with the ultrasound imaging device based on an image (e.g., the camera images 808 and 1010) captured by a camera (e.g., the cameras 150 and 801 and the optical capturing device 710). The image includes the subject's anatomy and the ultrasound imaging device positioned at the first position.

At step 1230, the method 1200 includes displaying, on a display (e.g., the UT/display 132 or the mobile device 920), an instruction to reposition the ultrasound imaging device from the first position to a second position based on the first motion control configuration and the positional information. The instruction can be displayed as shown in the display views 1000, 1110, 1120, and 1130.

In an embodiment, the first predictive network represents the first position based on a first coordinate system and the image captured by the camera represents the first position based on a second coordinate system. The method 1200 further include determining a coordinate system transformation (e.g., the transformation 822) between the first coordinate system and the second coordinate system based on the positional information. The coordinate system transformation may be similar to Equations (2) and (3) described above. The method 1200 further includes determining the instruction based on at least the first motion control configuration and the coordinate system transformation.

In an embodiment, the method 1200 further includes determining a second motion control configuration (e.g., the transformed or second motion control configuration 832) based on the first motion control configuration and the coordinate system transformation. The method 1200 further includes determining the instruction by applying at least one of a combining function (e.g., the combining function 840) to the first motion control configuration and the second motion control configuration or a comparison function to the first motion control configuration and the second motion control configuration.

In an embodiment, the ultrasound imaging device is coupled to a marker (e.g., the AR marker 804), where the image includes the marker. The method 1200 further includes determining the coordinate system transformation based on a relative position between the ultrasound imaging device and the marker (e.g., $markerT_{probe}$).

In an embodiment, the method 1200 further includes determining the coordinate system transformation based on a relative position between the camera and the subject's anatomy (e.g., $patientT_{camera}$), for example, when the camera is moving with respect to the subject's anatomy.

While the present disclosure describes the use of a camera (e.g., the cameras 150 and 801) or an optical capturing device (e.g., the optical capturing device 710) for tracking probe movements with respect to a subject under examination, the tracking can be achieved by using any suitable tracking device utilizing any suitable medium, such as suitable electromagnetic radiation (e.g., infrared, radio, etc.).

Aspects of the present disclosure can provide several benefits. For example, the use of a deep learning network to automate probe positioning guidance can assist a clinician in locating an optimal imaging view for an ultrasound examination. The rich features learnt by a deep learning network can provide probe position guidance independent of the patient's size and/or anatomy. The inclusion of the ROI detection and/or the image classification can limit the operations of the deep learning network to clinically relevant data and high-quality input images, and thus may reduce the size and/or complexity of the deep learning network and/or improve the motion prediction performance. The inclusion of the camera tracking in addition to the deep learning-based motion prediction can improve the accuracy of the automatic probe guidance and provide visual feedbacks to the clinician. The simultaneous displays of the camera view including the probe, the patient, and probe guidance instruction and the ultrasound view including a series of ultrasound images in real-time (e.g., as shown in the display views 1000, 1110, 1120, 1130, 1140, and 1150) can ease the workflow of an ultrasound examination and provide clear and easy to use instructions to the clinician. The present disclosure is suitable for use in transthoracic echocardiography (TTE), for example, to assist a user in accurate placement of an ultrasound transducer (e.g., in the right position and orientation with respect to a patient's heart anatomy). The present disclosure provides image-based guidance without relying on any external tracking devices, such as optical or electromagnetic tracking. Accordingly, the imaged-based guidance is suitable for implementation in low-cost portable devices.

Persons skilled in the art will recognize that the apparatus, systems, and methods described above can be modified in various ways. Accordingly, persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. A guidance system for obtaining an ultrasound image, comprising:
   a processor in communication with an ultrasound imaging device, a camera and a display, wherein the ultrasound imaging device is coupled to a marker, wherein the processor is configured to:
   obtain a first motion control configuration for providing a target image view of a subject's anatomy, wherein the first motion control configuration includes at least one of a first rotation or a first translation in a first coordinate system, wherein the first motion control configuration is determined based on a first predictive network, wherein, to obtain the first motion control configuration, the processor is configured to:
  receive, from the ultrasound imaging device, an ultrasound image representative of the subject's anatomy while the ultrasound imaging device is positioned at a first position; and
  apply the first predictive network to the ultrasound image to produce the first motion control configuration, wherein the first predictive network comprises a deep learning network;
determine positional information of the ultrasound imaging device with respect to the subject's anatomy based on an image captured by the camera, wherein the image includes the subject's anatomy, the ultrasound imaging device positioned at the first position, and the marker, wherein the positional information includes the first position in a second coordinate system;
determine a coordinate system transformation between the first coordinate system and the second coordinate system based on the positional information and a relative position between the ultrasound imaging device and the marker;
determine, based on the first motion control configuration and the positional information associated with the ultrasound imaging device, a second position to reposition the ultrasound imaging device; and
output, to the display, an instruction to reposition the ultrasound imaging device from the first position to the second position,
wherein the second position to reposition the ultrasound imaging device is distinct from a location that the instruction appears on the display.

2. The system of claim 1,
wherein the first motion control configuration is associated with a first motion between the first position and the second position in the first coordinate system,
wherein the processor is configured to:
  determine a second motion control configuration based on the first motion control configuration and the coordinate system transformation; and
  determine the second position based on the first motion control configuration and the second motion control configuration.

3. The system of claim 2, wherein the processor is configured to:
determine the second position by combining the first motion control configuration and the second motion control configuration.

4. The system of claim 2, wherein the processor is configured to:
determine the second position based on a comparison between the first motion control configuration and the second motion control configuration.

5. The system of claim 2, wherein the second motion control configuration includes at least one of a second rotation or a second translation in the second coordinate system and is associated with a second motion between the first position and the second position in the second coordinate system.

6. The system of claim 1, wherein the processor is configured to:
determine the coordinate system transformation based on a relative position between the camera and the subject's anatomy.

7. The system of claim 1, wherein the processor is configured to:
determine the coordinate system transformation based on a relative position between the camera and a marker positioned on the subject.

8. The system of claim 1,
wherein the processor is configured to output, to the display, the image including the subject's anatomy and the ultrasound imaging device,
wherein the instruction comprises a graphical representation of at least one of the first rotation or the first translation to reposition the ultrasound imaging device to the second position, and
wherein the graphical representation is overlaid on the image such that the graphical representation appears at the location on the display.

9. The system of claim 1, further comprising:
the camera; and
the display.

10. The system of claim 1, further comprising:
a mobile device including the camera, the processor, and the display.

11. The system of claim 1, wherein, to obtain the first motion control configuration, the processor is configured to:
apply the first predictive network to a region of interest (ROI) of the ultrasound image to produce the first motion control configuration.

12. The system of claim 11, wherein, to obtain the first motion control configuration, the processor is configured to do at least one of:
receive, from a user interface in communication with the processor, a selection of the ROI; or
determine the ROI based on a second predictive network.

13. The system of claim 1, wherein, to obtain the first motion control configuration, the processor is configured to:
apply the first predictive network to determine a region of interest (ROI) within the ultrasound image; and
determine the first motion control configuration based on the determined ROI.

14. A method of providing ultrasound imaging guidance, the method comprising:
obtaining a first motion control configuration for providing a target image view of a subject's anatomy, wherein the first motion control configuration includes a first rotation or a first translation in a first coordinate system, wherein the first motion control configuration is determined based on a first predictive network, wherein obtaining the first motion control configuration comprises:
  receiving, from an ultrasound imaging device coupled to a marker, an ultrasound image representative of the subject's anatomy while the ultrasound imaging device is positioned at a first position;
  applying the first predictive network to the ultrasound image to produce the first motion control configuration, wherein the first predictive network comprises a deep learning network;
determining positional information of the ultrasound imaging device with respect to the subject's anatomy based on an image captured by a camera, wherein the image includes the subject's anatomy, the ultrasound imaging device positioned at the first position, and the marker, wherein the positional information includes the first position in a second coordinate system;

determining a coordinate system transformation between the first coordinate system and the second coordinate system based on the positional information and a relative position between the ultrasound imaging device and the marker;

determining, based on the first motion control configuration and the positional information associated with the ultrasound imaging device, a second position to reposition the ultrasound imaging device; and displaying, on a display, an instruction to reposition the ultrasound imaging device from the first position to the second position, wherein the second position to reposition the ultrasound imaging device is distinct from a location that the instruction appears on the display.

15. The method of claim 14, wherein the first motion control configuration is associated with a first motion between the first position and the second position in the first coordinate system, and wherein the method further comprises:

determining the second position based on the first motion control configuration and the coordinate system transformation.

16. The method of claim 15, further comprising:

determining a second motion control configuration based on the first motion control configuration and the coordinate system transformation; and determining the second position by applying at least one of:
   a combining function to the first motion control configuration and the second motion control configuration; or
   a comparison function to the first motion control configuration and the second motion control configuration.

17. The method of claim 15, further comprising:

determining the coordinate system transformation based on a relative position between the camera and the subject's anatomy.

* * * * *